(12) United States Patent
Stuart

(10) Patent No.: US 9,480,532 B2
(45) Date of Patent: Nov. 1, 2016

(54) MANIPULATOR

(71) Applicant: J. Michael Stuart, Rio Rancho, NM (US)

(72) Inventor: J. Michael Stuart, Rio Rancho, NM (US)

(73) Assignee: MicroDexterity Systems, Inc., Albuquerque, NM (US)

( * ) Notice: Subject to any disclaimer, the term of this patent is extended or adjusted under 35 U.S.C. 154(b) by 464 days.

(21) Appl. No.: 13/943,512

(22) Filed: Jul. 16, 2013

(65) Prior Publication Data

US 2013/0304087 A1   Nov. 14, 2013

Related U.S. Application Data

(63) Continuation of application No. 12/976,721, filed on Dec. 22, 2010, now Pat. No. 8,491,604, which is a continuation of application No. 11/710,023, filed on Feb. 23, 2007, now Pat. No. 7,950,306.

(51) Int. Cl.
| | |
|---|---|
| *A61B 19/00* | (2006.01) |
| *B25J 9/10* | (2006.01) |
| *B25J 17/02* | (2006.01) |
| *B25J 9/00* | (2006.01) |

(52) U.S. Cl.
CPC ........... *A61B 19/2203* (2013.01); *A61B 34/30* (2016.02); *A61B 34/35* (2016.02); *A61B 34/70* (2016.02); *A61B 34/75* (2016.02); *A61B 34/76* (2016.02); *A61B 34/77* (2016.02); *B25J 9/0072* (2013.01); *B25J 9/106* (2013.01); *B25J 17/0266* (2013.01); *A61B 2034/304* (2016.02); *A61B 2090/064* (2016.02); *Y10S 901/19* (2013.01); *Y10T 74/20305* (2015.01); *Y10T 74/20311* (2015.01); *Y10T 74/20323* (2015.01); *Y10T 74/20329* (2015.01); *Y10T 403/32* (2015.01); *Y10T 403/32049* (2015.01)

(58) Field of Classification Search
CPC ............................................. A61B 2034/304
See application file for complete search history.

(56) References Cited

U.S. PATENT DOCUMENTS

| | | | | |
|---|---|---|---|---|
| 5,053,687 | A * | 10/1991 | Merlet | B25J 17/0216 318/566 |
| 6,116,844 | A * | 9/2000 | Hayward | B25J 9/106 414/680 |
| 6,540,471 | B1 * | 4/2003 | Brogårdh | B25J 9/104 414/729 |

* cited by examiner

*Primary Examiner* — Terence Boes
(74) *Attorney, Agent, or Firm* — Leydig, Voit & Mayer, Ltd.

(57) ABSTRACT

A manipulator, such as for use in medical procedures, is provided. The manipulator includes a body and a first actuator system connected to the body at a first attachment point and capable of moving the first attachment point with at least three degrees of freedom. A second actuator system is connected to the body at a second attachment point and capable of moving the second attachment point with at least three degrees of freedom. A third actuator system is integrated with the body and is capable of moving at least a portion of the body with at least one degree of freedom.

10 Claims, 6 Drawing Sheets

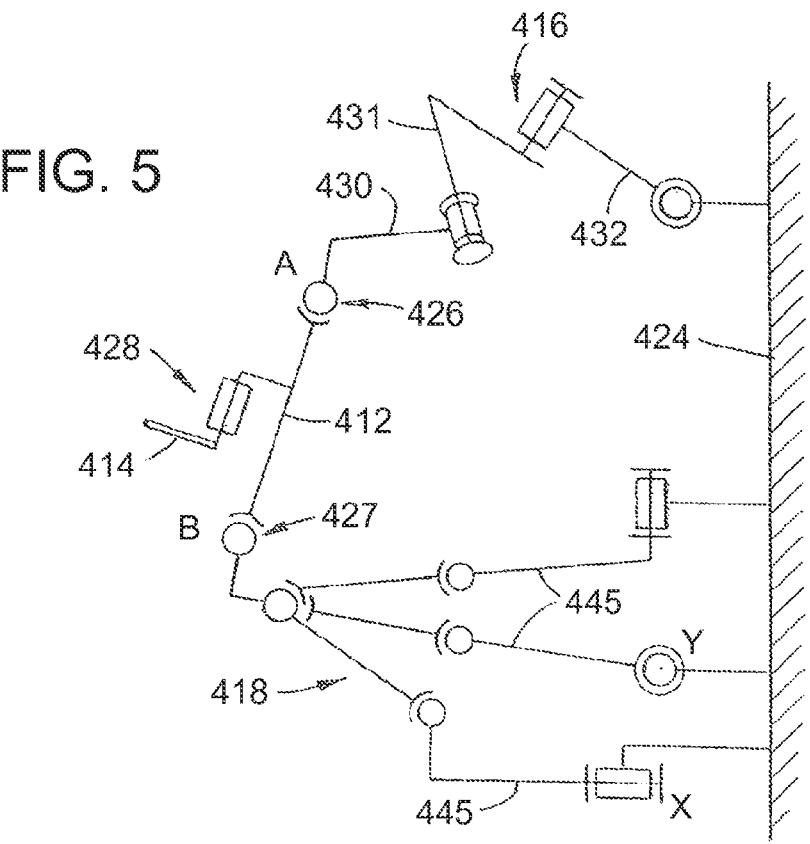

MANIPULATOR

BACKGROUND OF THE INVENTION

Conventional devices which are used to perform very complex and/or physically demanding surgical procedures like neurosurgery, spine surgery, ear surgery, head and neck surgery, hand surgery and minimally invasive surgical procedures have a number of drawbacks as it relates to the dexterity of the surgeon. For example, the surgeon can easily become fatigued by the need to manually support the surgical device during its use. Additionally, the surgeon may have to orient his hands in an awkward position in order to operate the device. Furthermore, conventional devices used in such surgical procedures can produce angular magnification of errors. As a result, a surgeon has considerably less dexterity and precision when performing an operation with such surgical devices than when performing an operation by traditional techniques in which the surgeon grasps a tool directly.

Accordingly, there is an increasing interest in the use of powered manipulators, such as robotic and master-slave manipulators for supporting and manipulating surgical tools during medical procedures. Such manipulators can provide a number of advantages to both patients and medical practitioners. In particular, a master/slave controlled manipulator can enhance the dexterity of the surgeon/operator so as to allow the surgeon to manipulate a medical tool with greater dexterity than he could if he was actually holding the tool in his hands. A manipulator can also reduce the fatigue experienced by a surgeon, since it eliminates the need for the surgeon to physically support the medical tool or device during its use. Additionally, the surgeon can let go of the manipulator and perform other tasks without the medical tool undergoing movement, which increases the efficiency of the surgeon and can reduce the number of individuals that are necessary to perform a particular procedure. Thus, manipulators can allow medical procedures to be performed much more rapidly, resulting in less stress on the patient.

However, many manipulators, including those having six degrees of freedom, have some drawbacks in that, in certain orientations, the amount of torque that the manipulator can apply is limited. This restricts the work that can be done by the manipulator in such orientations. Moreover, some manipulators have singularity points within their operational envelopes. At these singularity points, two or more manipulator joints become redundant and fewer degrees of the freedom can be exercised. This can cause a manipulator mechanism to become locked or impeded such that it can no longer move freely.

BRIEF SUMMARY OF THE INVENTION

The invention provides a manipulator that includes a body and a first actuator system connected to the body at a first attachment point and capable of moving the first attachment point with at least three degrees of freedom. A second actuator system is connected to the body at a second attachment point and capable of moving the second attachment point with at least three degrees of freedom. A third actuator system is integrated with the body and is capable of moving at least a portion of the body with at least one degree of freedom.

The invention further provides a manipulator including first and second actuator systems each including three or more powered actuators with each of the three or more powered actuators being arranged in series relative to the others. Each powered actuator is capable of actuating a separate movement of at least a portion of the respective actuator system without any movement of the other actuator system. A body is supported by the first and second actuator systems at first and second attachment points, respectively, such that the first and second actuator systems are capable of manipulating the body in five degrees of freedom. A third actuator system has first and second ends. The first end of the third actuator system is attached to the body, wherein the second end is movable relative to the body with at least one degree of freedom without any movement of either the first or second actuator system.

The invention further provides a manipulator including first and second actuator systems each including three or more powered actuators. Both the first and second actuator systems include first and second powered actuators arranged in series and a four-bar linkage arranged in series with the first and second powered actuators. The four-bar linkage is driven by a third powered actuator. A body is supported by the first and second actuator systems at first and second attachment points, respectively, such that the first and second actuator systems are capable of manipulating the body in five degrees of freedom.

The invention further provides a manipulator including first and second actuator systems each including three or more powered actuators. Each powered actuator is capable of actuating a separate movement of at least a portion of the respective actuator system without any movement of the other actuator system. A body is supported by the first and second actuator systems at first and second attachment points, respectively, such that the first and second actuator systems are capable of manipulating the body in five degrees of freedom wherein the first attachment point comprises a two degree of freedom joint and the second attachment point comprises a three degree of freedom joint. A third actuator system has first and second ends. The first end of the third actuator system is attached to the body, wherein the second end is movable relative to the body with at least one degree of freedom without any movement of either the first or second actuator system.

BRIEF DESCRIPTION OF THE SEVERAL VIEWS OF THE DRAWING(S)

FIG. 5 is a schematic view of an alternative embodiment of a manipulator according to the present invention that includes a three degree of freedom rotary axis serial actuator and a three degree of freedom rotary axis parallel actuator.

FIG. 6 is a schematic view of a further alternative embodiment of a manipulator according to the present invention that includes a three degree of freedom mixed architecture serial actuator and a three degree of freedom mixed architecture parallel actuator.

DETAILED DESCRIPTION OF THE INVENTION

Figure 1:
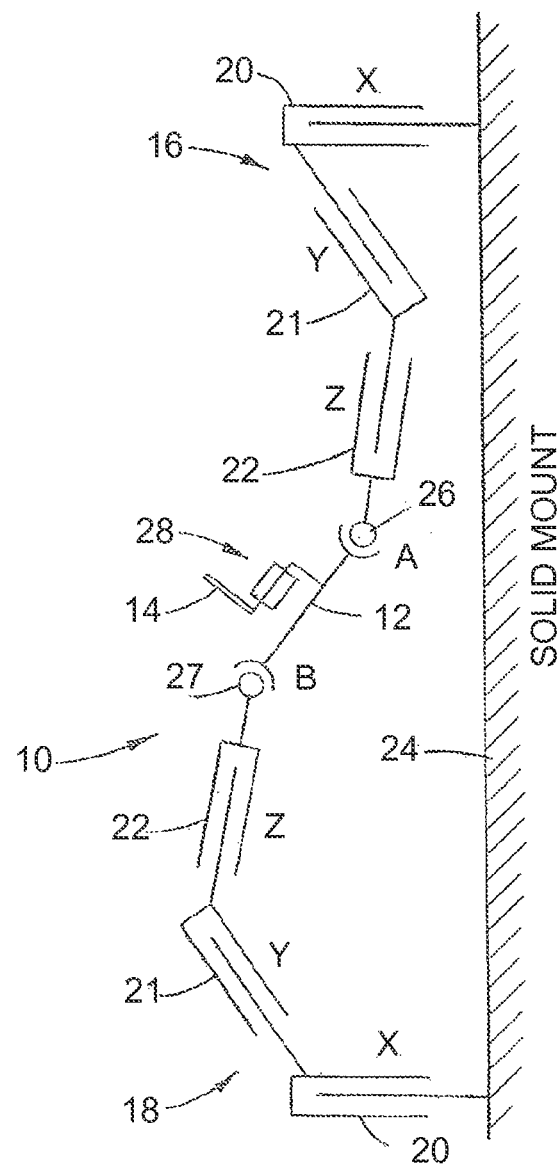
FIG. 1 is a schematic view of an exemplary manipulator constructed in accordance with the present invention that includes two three degree of freedom linear axis serial actuators.

Referring now more particularly to FIG. 1 of the drawings, there is shown an illustrative embodiment of a manipulator constructed in accordance with the present invention. The illustrated manipulator 10 can interchangeably support and move a body with six degrees of freedom. In this case, the moving body can comprise a support member 12 that carries an end effector, e.g. a medical tool holder or mount 14. As will be appreciated, the invention is not limited to any particular type or form of moving body. In this regard, the invention is also not limited to any particular type of medical tool, tool holder or support structure rather any suitable tool and/or tool support can be used with the manipulator including, but not limited to, needle holders, staple or clamp appliers, probes, scissors, forceps, cautery, suction cutters, dissectors, drills, saws, lasers, ultrasonic devices and diagnostic devices. The tools can be reusable, limited reuse or disposable. If the medical tool has moving parts that are conventionally human powered, the manipulator 10 can be adapted to accommodate an actuator dedicated to powering the tool such as for example an electric, pneumatic or hydraulic actuator.

While the present invention is described in connection with performing complex medical procedures, the manipulator of the present invention is not limited to such applications. Rather, the manipulator of the present invention can be used in any application involving dexterous tasks. For example, it can be used in applications involving the remote manipulation of hazardous materials. It can also be used in complex assembly or repair operations to perform autonomous, but repetitive, tasks normally done by humans.

In order to provide dexterity enhancement for an operator/surgeon in performing surgical and certain interventional radiology procedures, the manipulator 10 can be used as a slave robot in a master-slave robotic system. The manipulator 10 can also be used as a master robot in such a system. In a master-slave robotic system, a surgeon/operator provides position input signals to the "slave" manipulator via a master or haptic interface which operates through a controller or control console. Specifically, with the manipulator 10 of the present invention serving as the slave robot, the surgeon indicates the desired movement of the tool held by the manipulator 10 through the use of an input device on the haptic interface such as a six degree of freedom tool handle with or without force feedback, joystick, foot pedal or the like. The haptic interface relays these signals to the controller, which, in turn, applies various desired predetermined adjustments to the signals prior to relaying them to the slave manipulator. Any haptic interface having six or more degrees of freedom (DOF) can be used to control the manipulator 10 via the controller. Examples of haptic interfaces or masters which can be used with the present invention include the Freedom 6S available from MPB Technologies of Montreal, Canada, and other haptic interfaces commercially available from Sensable Technology of Cambridge, Mass. and MicroDexterity Systems of Albuquerque, N.Mex.

Based on the signals provided by the controller, the manipulator 10 executes the desired movement or operation of the tool. Thus, any desired dexterity enhancement can be achieved by setting up the controller to perform the appropriate adjustments to the signals sent from the haptic interface. For example, this can be accomplished by providing the controller with software which performs a desired dexterity enhancement algorithm. Software dexterity enhancement algorithms can include position scaling (typically downscaling), force scaling (up-scaling for bone and cartilage, downscaling for soft tissue), tremor filtering, gravity compensation, programmable position boundaries, motion compensation for tissue that is moving, velocity limits (e.g., preventing rapid movement into brain, nerve or spinal cord tissue after drilling through bone), and, as discussed in greater detail below, image referencing. These and other examples of possible algorithms are well known in the field of robotics and described in detail in published literature. The ZMP SynqNet® Series Motion Controllers which employ the SynqNet system and are available from Motion Engineering of Santa Barbara, Calif. are one example of a suitable controller for use with the present invention (see www.synqnet.org and www.motioneng.com). Another example of a suitable controller is the Turbo PMAC available from Delta Tau Data Systems of Northridge, Calif.

To effect movement of the support member 12 in space, the manipulator 10 includes first and second actuator systems 16, 18 each of which connects to the support member 12 at a respective attachment point. Each actuator system 16, 18 comprises a separate, independent three degree of freedom manipulator. The first and second actuator systems 16, 18 can be any type of three degree of freedom actuator system. More specifically, any combination of three rotary or three linear actuators can be used to form each of the actuator systems 16, 18. For instance, as shown in FIG. 1, the first and second actuator systems 16, 18 could comprise simple linear axis serial actuators.

In the FIG. 1 embodiment, each of the first and second actuator systems 16, 18 comprises three linear sliding joints or actuators 20, 21, 22. Each of the sliding joints/actuators 20, 21, 22 translates or slides along a respective Cartesian coordinate axis, i.e. x, y or z. In this case, each of the actuator systems includes an x-axis linear joint/actuator 20 that has one end connected to a solid mount 24 and a second end connected to a y-axis linear joint/actuator 21. The opposite end of the y-axis linear joint/actuator 21 is, in turn, connected to a z-axis linear joint/actuator 22. The z-axis linear joint/actuator 22 of each of the first and second actuator systems 16, 18 connects at a respective attachment point to the support member 12. A "seventh" degree of freedom is provided by a rotary joint/actuator 28 that is integrated with the support member 12 and is capable of producing rotary movement of the tool mount 14 relative to the support member 12. The rotary joint/actuator 28 integrated with the support member 12 makes up for a degree of freedom from the first and second actuator systems that is "lost" because of the fixed length of the support member 12.

In the embodiment illustrated in FIG. 1, the attachment points of the first and second actuator systems each comprise a joint 26, 27, such as a spherical joint, having three rotary degrees of freedom. However, as discussed below in connection with the embodiment of FIGS. 7 and 8, according to one preferred arrangement, the attachment point for one of the actuator systems can comprise a joint (e.g., a gimbals joint) that has only two rotary degrees of freedom while the other attachment point comprises a joint (e.g., a spherical joint) having three rotary degrees of freedom. Such an arrangement eliminates the free rotation of the support member that can occur if two three degree of freedom spherical joints are used. While movement of the first and second actuator systems 16, 18 can cause some rotation of the support member 12 even with such an arrangement, the rotation is predictable and can be addressed with corresponding movements of the first and second actuator systems and the rotary joint/actuator 28. The joints can have any desired construction that provides the necessary degrees of rotary freedom. Moreover, single joints at the attachment points can be replaced with multiple joints that collectively provide equivalent degrees of freedom.

Figure 2:
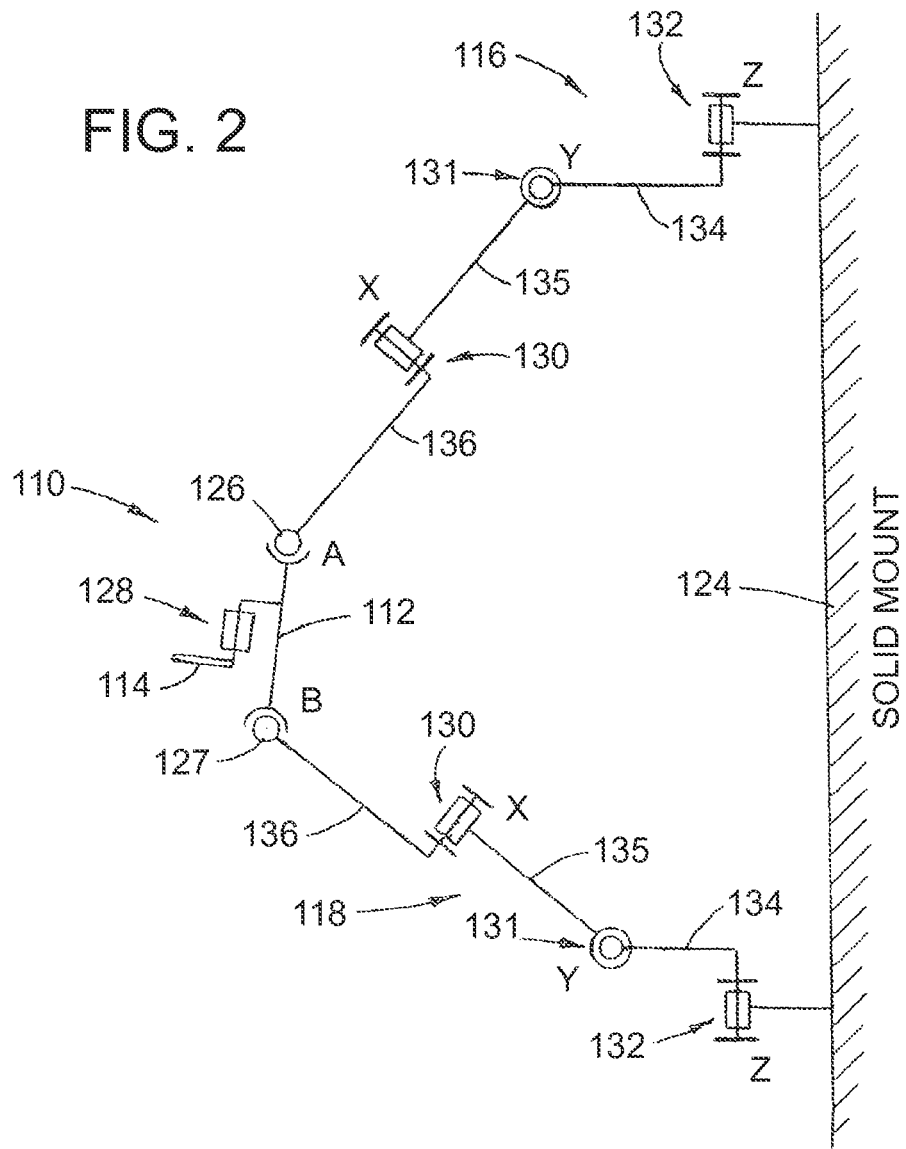
FIG. 2 is a schematic view of an alternative embodiment of a manipulator according to the present invention that includes two three degree of freedom rotary axis serial actuators.

An alternative embodiment in which three rotary joint/actuators 130, 131, 132 are employed in the first and second actuator systems 116, 118 as opposed to linear joints/actuators is shown in FIG. 2. In the embodiment of FIG. 2, elements similar to those found in the FIG. 1 embodiment are given corresponding reference numbers in the 100s. As the case with the FIG. 1 embodiment, the rotary joint/actuators 130, 131, 132 are in a serial arrangement with each rotary joint/actuator rotating about a respective Cartesian coordinate axis, i.e. x, y or z. In the arrangement illustrated in FIG. 2, each of the first and second actuator systems 116, 118 includes an z-axis rotary joint/actuator 132 that is connected to a solid mount 124. The output shaft of the z-axis rotary joint/actuator 132 is connected to a first link 134 that extends to a y-axis rotary joint/actuator 131. The output shaft of the y-axis rotary joint/actuator 131, in turn, connects via a second link 135 to a x-axis rotary joint/actuator 130, which has an output shaft that connects to a third link 136 that connects at a respective attachment point to the support member 112. With each actuator systems 116, 118, the angles of the three rotary joints/actuators 130, 131, 132 define the positions of the two attachment points. In this instance, both attachment points comprise three degree of rotary freedom spherical joints 126, 127. As with the FIG. 1 embodiment, a seventh degree of freedom is provided via a rotary joint/actuator 128 integrated with the support member 112 for rotating a tool mount 114 relative to the support member.

Figure 3:
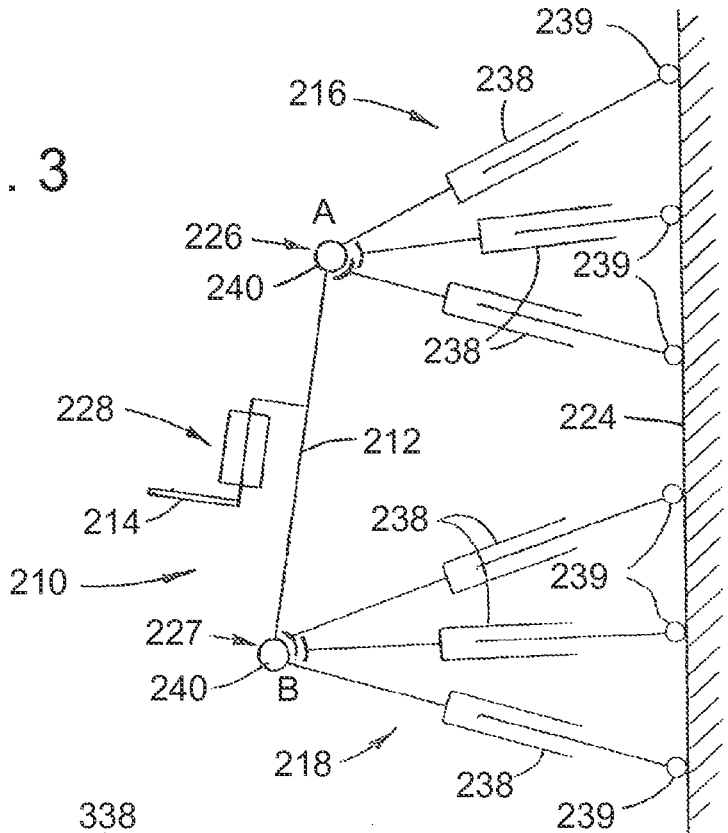
FIG. 3 is a schematic view of another alternative embodiment of a manipulator according to the present invention that includes two three degree of freedom linear axis parallel actuators.

A further embodiment that employs three degree of freedom parallel, as opposed to serial, actuators as the first and second actuators systems is shown in FIG. 3. In FIG. 3, elements similar to those found in the FIGS. 1 and 2 embodiments are given corresponding reference numbers in the 200s. Specifically, in the FIG. 3 embodiment, each of the first and second actuator systems 216, 218 comprises three linear joints/actuators 238 arranged in parallel. Each of the linear joints/actuators 238 is connected at one end to a solid mount 224 via a respective three degree of rotary freedom spherical joint 239. The other end of the each of the linear joint actuators 238 is connected to a fixed sphere 240 so as to form a tripod arrangement in which the tip, i.e. the fixed sphere, can be moved in space. The fixed sphere is part of a spherical joint 226, 227 that defines the attachment point to the support member 212. In this case, one of the three linear joint actuators 238 of each actuator system 216, 218 is rigidly connected to the fixed sphere while the other two are connected to the sphere in such a way that they each can rotate about the sphere with three degrees of freedom. Again, a seventh degree of freedom is provided via a rotary joint/actuator 228 integrated with the support member 212 for rotating a tool mount 214 relative to the support member 212.

Figure 4:
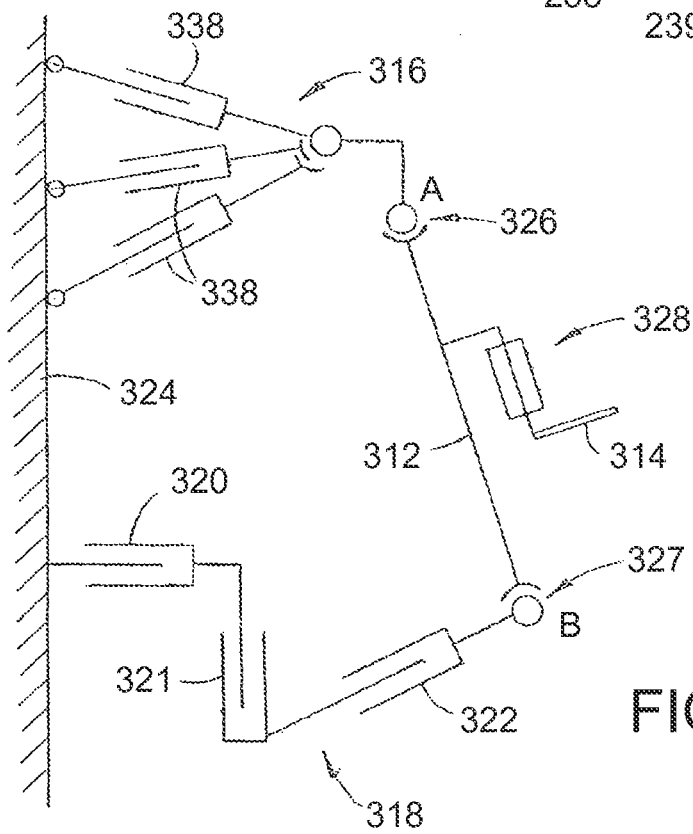
FIG. 4 is a schematic view of a further alternative embodiment of a manipulator according to the present invention that includes a three degree of freedom linear axis parallel actuator and a three degree of freedom linear axis serial actuator.

As shown in FIGS. 4-5, the first and second actuator systems can have different configurations. More specifically, in the embodiment of the invention shown in FIG. 4, the first actuator system 316 comprises a three degree of freedom parallel linear actuator having a tripod configuration like that used for the first and second actuator systems in the embodiment of FIG. 3. In FIG. 4, elements similar to those found in the embodiments of FIGS. 1-3 are given corresponding reference numbers in the 300s. In the FIG. 4 embodiment, the second actuator system 318 comprises a three degree of freedom serial linear actuator (with linear actuators 320, 321, 322) like that used in the embodiment of FIG. 1. Again, each of the actuator systems 316, 318 connects to the support member 312 at a respective attachment point comprising a spherical joint 326, 327 and a rotary joint/actuator is integrated with the support member 312 for rotating a tool mount 314 relative to the support member to provide the seventh degree of freedom.

In the embodiment of FIG. 5, elements similar to those found in the embodiments of FIGS. 1-4 are given corresponding reference numbers in the 400s. In FIG. 5, the first actuator system 416 comprises a three degree of freedom serial rotary actuator (with rotary actuators 430, 431, 432) like that used in the embodiment of FIG. 2 and the second actuator system 418 comprises a three degree of freedom parallel rotary actuator, which is generally similar to the three degree of freedom parallel tripod actuators of FIG. 3 but with rotary joints/actuators 445 instead of linear joints/actuators. In particular, the three degree of freedom parallel rotary second actuator system 418 includes three legs each of which is connected to a respective rotary joint/actuator 445. Each rotary joint/actuator 445 is connected to the solid mount 424 and rotates about a respective one of the Cartesian coordinate axes, i.e. x, y and z. Again, each of the actuator systems 416, 418 connects to the support member 412 at a respective attachment point comprising a spherical joint 426, 427 and a rotary joint/actuator 428 is integrated with the support member 412 for rotating a tool mount 414 relative to the support member to provide the seventh degree of freedom.

As shown in the embodiment of FIG. 6, the individual first and second actuator systems 516, 518 can have mixed architectures including both linear and rotary joints/actuators. In FIG. 6, elements similar to those found in the embodiments of FIGS. 1-5 are given corresponding reference numbers in the 500s. In the FIG. 6 embodiment, the first actuator system 516 is a serial arrangement that includes a z-axis rotary joint/actuator 547 having an output shaft connected to a link that connects to a linear joint/actuator 548 that, in turn, is connected to a y-axis rotary joint/actuator 549. The second actuator system 518 is a parallel tripod arrangement consisting of one leg with a rotary joint/actuator 551 and two legs with linear joints/actuators 552. Again, each of the actuator systems 516, 518 connects to the support member 512 at a respective attachment point comprising a spherical joint 526, 527 and a rotary joint/actuator 528 is integrated with the support member 512 to rotate a tool mount 514 relative to the support member to provide the seventh degree of freedom. The FIG. 6 embodiment illustrates that any combination of rotary and linear actuators that provides the desired three degrees of freedom can be used to form the first and second actuator systems.

Figure 7:
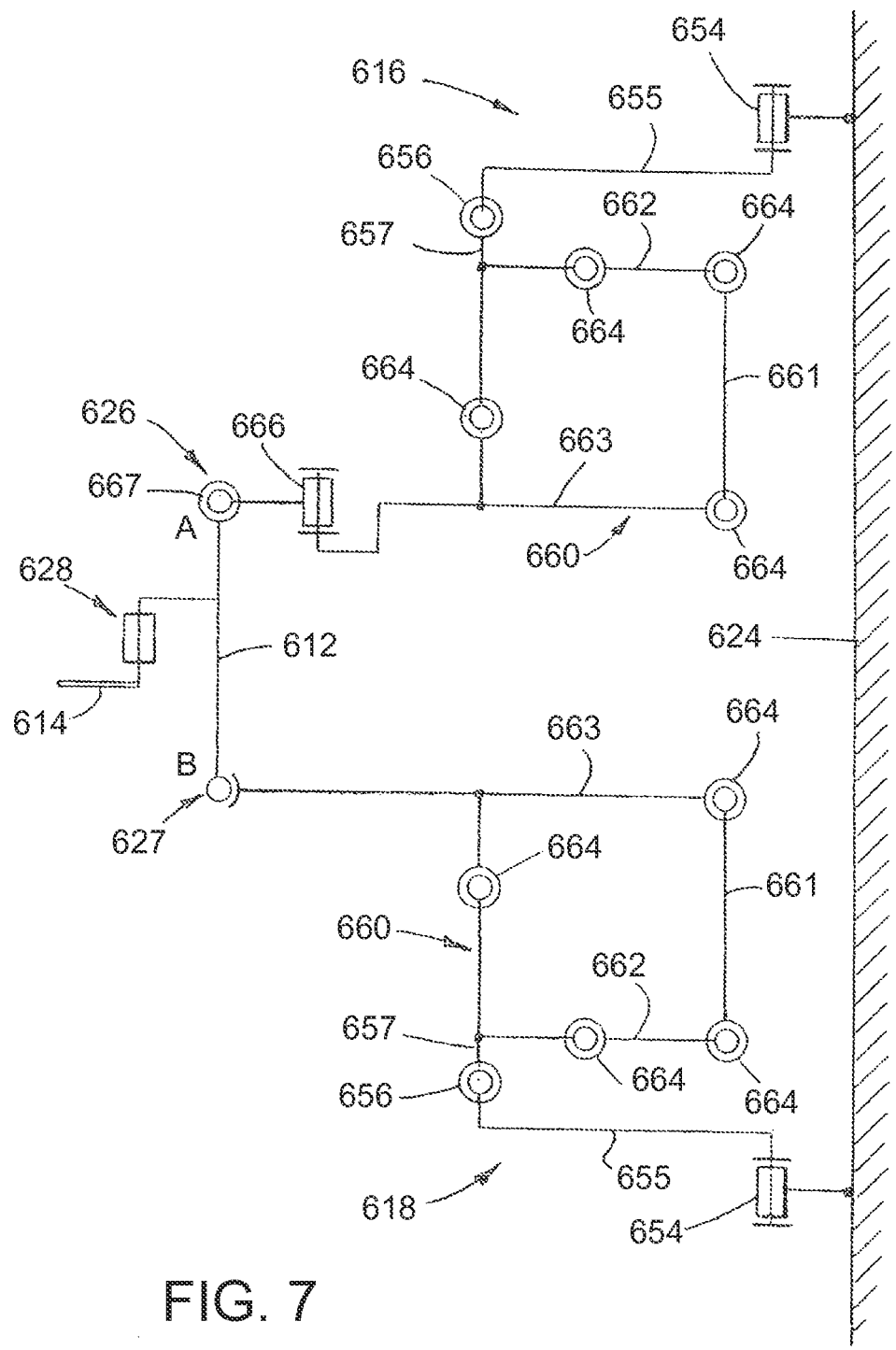
FIG. 7 is a schematic view of another embodiment of a manipulator according to the present invention.

A preferred hybrid serial/parallel manipulator arrangement is schematically illustrated in FIG. 7. In FIG. 7, elements similar to those found in the embodiments of FIGS. 1-6 are given corresponding reference numbers in the 600s. In the FIG. 7 embodiment, each of the first and second actuator systems 616, 618 is a three degree of freedom serial arrangement using rotary joints/actuators. Referring specifically to FIG. 7 of the drawings, each of the first and second actuator systems 616, 618 includes a first rotary joint 654 that is connected to a solid mount 624. The output shaft of the first rotary joint 654 comprises a first link 655 that connects to a second rotary joint 656. The second rotary joint 656 has a rotational axis that extends perpendicular to the rotational axis of the first rotary joint 654. The output of the second rotary joint 656 comprises a second link 657 that defines one of the side legs of a four-bar mechanical linkage 660. The four-bar linkage 660 of each of the actuator systems includes 2 side legs 657, 661 and upper and lower arms 662, 663. The four bars, i.e. the two side legs and the upper and lower arms 657, 661, 662, 663, of the 4-bar mechanical linkage 660 are interconnected via rotary joints 664 each having one degree of rotational freedom, e.g. pinned pivots. The rotational axes of the four rotary joints 664 in the four-bar linkage 660 extend parallel to each other and to the rotational axis of the second rotary joint 656.

The lower arm 663 of each of the four-bar linkages 660 connects to the support member 612 at a respective connection point. In this case, the upper connection point includes two rotary pivots 666, 667 having rotational axes extending perpendicular to each other so as to provide the connection point with two rotational degrees of freedom and the lower connection point includes a spherical joint 627 with three degrees of rotational freedom. As with the embodiments of FIGS. 1-6, the first and second actuator systems 616, 618 can provide a total of six degrees of freedom and a seventh degree of freedom is provided by a rotary joint/actuator 628 that is integrated with the support member 612 for rotating a tool mount 614 relative to the support member.

Figure 8:
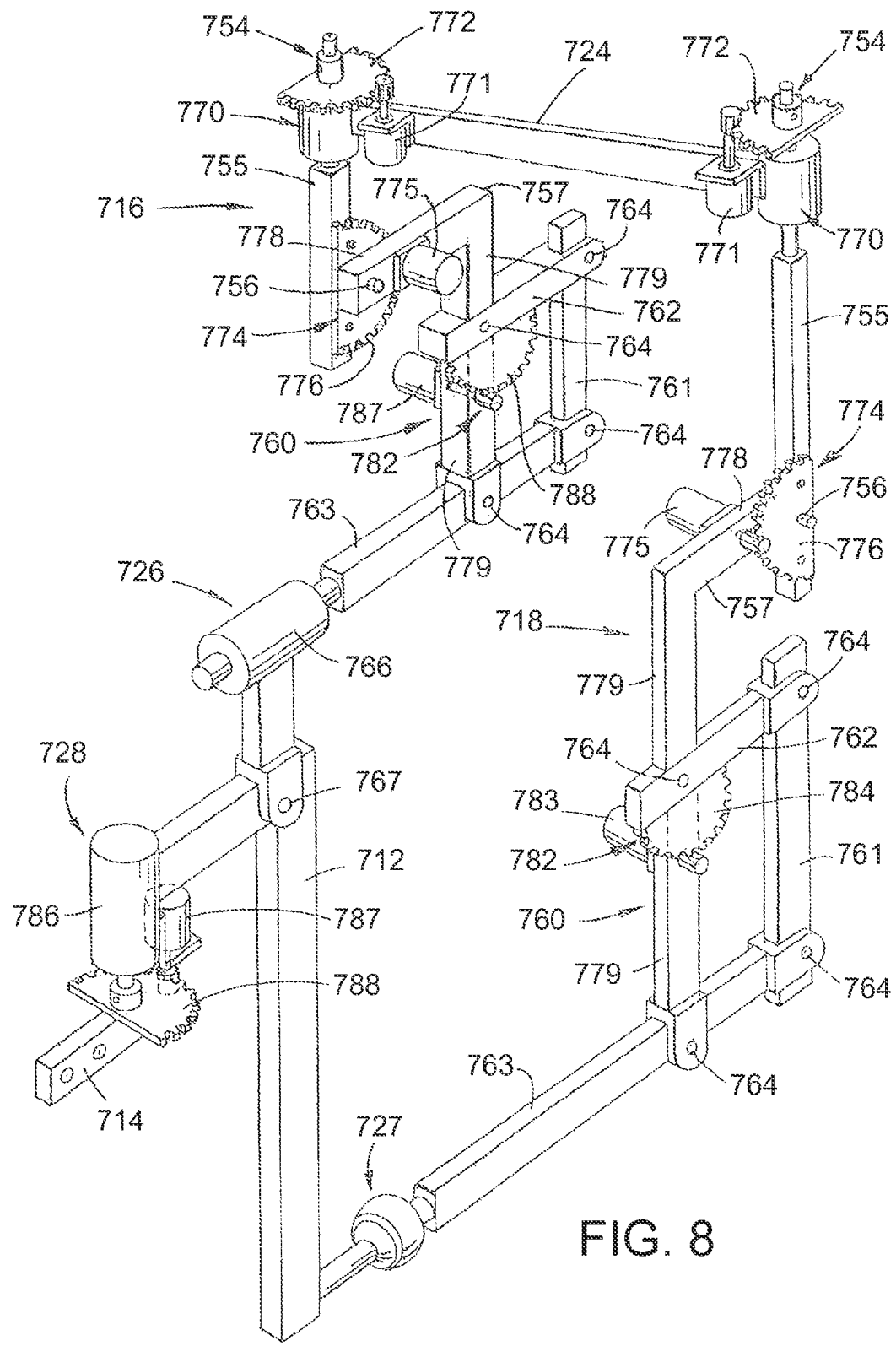
FIG. 8 is a perspective view of an illustrative manipulator having the configuration shown schematically in FIG. 7.

The arrangement of FIG. 7 is better understood with reference to FIG. 8, which illustrates a more specific embodiment of a manipulator having the configuration shown schematically in FIG. 7. In FIG. 8, elements similar to those found in the embodiments of FIGS. 1-7 are given corresponding reference numbers in the 700s. The embodiment of FIG. 8 includes a header 724 serving as a solid mount that connects the first and second actuator systems 716, 718 together. In particular, both the first and second actuator systems 716, 718 include a first rotary joint/actuator 770 that includes a rotatable first link 755 that extends, in this case, downward from the header 724. In the illustrated embodiment, the first link 755 rotates about its longitudinal axis which extends perpendicular to the header 724. To this end, the first rotary joint/actuator 770 of each of the first and second actuator systems 716, 718 includes a rotary pivot 754. The first rotary joint/actuator 770 further includes a mechanism for driving rotation of the respective first link 755 relative to the header 724. In this instance, the rotating mechanism comprises a gear drive that includes a motor 771 with a geared output shaft that is mounted on the header 724 and acts on a gear 772 supported on the first link 755.

The first link of each of the first and second actuator systems 716, 718 connects to a second link 757 having, in this case an L-shaped configuration and which forms part of a four-bar mechanical linkage 760. The first link 755 connects to the second link 757 via a second rotary joint/actuator 774. The second rotary joint/actuator 774 includes a first pinned pivot 756 that permits the second link 757 to rotate relative to the first link 755 about an axis that extends perpendicular to the rotational axis of the first link 755. The second rotary joint/actuator 774 further includes a mechanism for rotating the second link 757 relative to the first link 755 that comprises a motor 775 with a geared output shaft that is mounted on the second link 757 and acts on a gear 776 supported on the first link 755.

The L-shaped second link includes an upper portion 778 that connects to the first link 755 and a lower portion 779 that, as previously noted, forms part of a four-bar mechanical linkage 760. In the illustrated embodiment, the four-bar linkage 760 comprises the lower portion 779 of the second link 757 which defines one side leg of the linkage, a second side leg 761 and upper and lower arms 762, 763. The second side leg 761 extends parallel to the lower portion 779 of the second link 757 and is connected thereto by the upper arm 762 and the lower arm 763. More specifically, the upper arm 762 is pivotally connected to the lower portion 779 of the second link 757 and to the second side leg 761 by respective pinned pivots 764. Similarly, the lower arm 763 is pivotally connected to the lower portion 779 of the second link 757 and the second side leg 761 by respective pinned pivots 764. The rotational axes of the four pinned pivots 764 in the four-bar mechanical linkage 760 extend parallel to each other and to the rotational axis of the pinned pivot 756 connecting the first and second links 755, 757 and in a plane perpendicular to the plane containing the rotational axes of the rotary pivot 754 connecting the first link 755 and the header 724.

In the illustrated embodiment, the four-bar linkage 760 of each of the first and second actuator systems 716, 718 is driven by a third rotary joint/actuator 782 comprising the pinned pivot 764 between the lower portion 779 of the second link 757 and the upper arm 762 and a gear drive that includes a motor 783 with a geared output shaft that is mounted on the lower portion 779 of the second link 757. The geared output shaft of the motor 783 acts on a gear 784 mounted on the upper arm 762 so as to drive pivotal movement of the lower portion 779 of the second link 757 relative to the upper arm 762 and, in turn, movement of the entire four-bar linkage 760. While the drive for the four-bar linkage 760 could be arranged at any of the four pivots 764 of the linkage, arranging the drive where shown in the embodiment of FIG. 8 helps minimize the rotational inertia of the manipulator by keeping the various motors close to a central point. Thus, less torque is required for each individual motor to move the other motors and/or hold them in a particular position.

With the first and second actuator systems 716, 718, the third rotary joint/actuator 782, including the gear drive at the pinned pivot 764 joining the upper arm 762 and the lower portion 779 of the second link 757, generally controls the tilt of the lower arm 763. The second rotary joint/actuator 774, including the gear drive at the pinned pivot 756 joining the first and second links 755, 757, generally controls the tilt of the entire lower portion of the respective actuator system including the position of the driven pinned pivot 764 of the four-bar linkage 760. Thus, to make the lower arm 763 move in a linear direction (i.e., in a direction coincident with its longitudinal axis) in the plane in which it is illustrated in FIG. 8, the two gear drives of the second and third rotary joints/actuators 774, 782 must be controlled so that they work together in tandem. For example, to produce a linear movement of the lower arm 763, the gear drive of the second rotary joint/actuator 774 can be used to pivot the second link 757 relative to the first link 755 and thereby generally sweep the lower arm 763 back and forth while the gear drive of the third rotary joint/actuator 782 rotates the upper arm 763 relative to the second link 757 in a direction counter to that produced at the pinned pivot 756 of the second rotary joint/actuator in order to keep the lower arm 763 level. To move the lower arm 763 in a linear direction in a different plane than that illustrated in FIG. 8, requires the manipulation of the drive motors of all three of the rotary joints/ actuators in the respective actuator system 716, 718.

The lower arm 763 of each of the first and second actuator systems 716, 718 extends to a support member 712 to which it is connected. In the illustrated embodiment, the lower arm 763 of the first actuator system 716 connects to the support member 712 via a rotary pivot 766 and a pinned pivot 767 so as to provide two degrees of rotational freedom. The lower arm 763 of the second actuator system 718, in turn, connects to the support member 712 via a spherical joint 727 that provides three degrees of rotational freedom. As noted above, limiting the one of the connection points of the first and second actuator systems to a two degree of freedom joint system such as with the first actuator system 716 in the embodiment of FIG. 8 helps prevent free rotation of the support member 712, which can occur if two three degree of freedom spherical joints are used In the illustrated embodiment, the support member 712 has an L-shaped configuration including a first longer leg to which the lower arms 763 of the first and second actuator systems 716, 718 are connected and a second shorter leg to which a tool mount 714 is connected. For rotating the tool mount 714 relative to the support member, a rotary joint/ actuator 728 is integrated with the support member 712. The rotary joint/actuator 728 integrated with the support member 712 includes a rotary pivot 786 that connects the tool mount 714 to the support member 712. In this instance, the rotary pivot 786 has a rotational axis that extends parallel to the rotational axis of the rotary pivots 754 connecting the first links 755 of the first and second actuator systems 716, 718 to the header 724. For driving rotation of the tool mount 714 relative to the support member 712, the rotary joint/actuator 728 includes a gear drive which includes a motor 787 with a geared output shaft that acts on a gear 788 connected to the tool mount 714. The rotation of the tool support 712 produced via the gear drive and rotary pivot 786 is independent of any rotation of the tool support 712 that may be produced via the first and second three degree of freedom actuator systems 716, 718.

In the embodiment of FIG. 8, the load on which the first and second actuator systems are acting includes the support member 712, the tool mount 714 and the tool mounted to the tool mount 714. To help minimize the size of the motors that are required as well as the power that must be applied to maintain the manipulator in a given position, the first and second actuator systems can be configured so as to help counterbalance this load. In particular, the individual actuator systems can be arranged or configured such that with one or more of the rotary joints/actuators parts of the respective actuator system are arranged on the side of the rotational axis defined by that rotary joints/actuators opposite the side on which the load or other parts of the actuator system are arranged.

For example, with respect to the embodiment of FIG. 8, the four bar mechanism is not required to achieve three degrees of freedom of each of the actuator systems. Instead, the gear drive of the third rotary joint/actuator 782 at the pinned pivot 764 between the lower portion 779 of the second link 757 and the upper arm 762 could be relocated to the joint 764 between the lower portion 779 and the lower arm 763, in which case the upper arm 762 and second side leg 761 could be eliminated. However, such an arrangement is not well balanced as the weight of the support member 712, tool support 714 and tool will create a moment that will pull downwards on the distal end of the lower arm 763. Because it is arranged on the opposite side of the rotational axis defined by the third rotary joint/actuator, the four-bar linkage in the embodiment of FIG. 8 provides a counterbalance to this moment, which reduces the overall load on the gear drive. In a similar fashion, the actuator systems could be arranged such that some is arranged behind the rotational axis defined by the first rotary joint/actuator 770 (such as the case with the first actuator system 716) to provide a counterbalance to the load (support member 712, tool mount 714 and tool) which is arranged in front of the axis.

In the embodiment shown in FIG. 8, each of the first and second actuator systems 716, 718 includes three rotary joint/actuators 770, 774, 782 (i.e. rotary joint and gear drive combinations) and thus can move the end point of its respective lower arm 763 with three degrees of freedom. Thus, the first and second actuator systems 716, 718 provide a total of six degrees of freedom. The rotary joint/actuator 728 integrated with the support member 712 provides a seventh degree of freedom. While the manipulator has seven degrees of freedom, one degree of freedom is made redundant by the structure of the manipulator including the fixed length of the support member 712. Thus, the resulting seven degree of freedom manipulator provides coordinated motion of the tool mount 714 in six degree of freedom space. While gear drives are shown for each of the rotary joints/actuators in the embodiment of FIG. 8, other drive systems also can be used. For example, another preferred drive system for producing rotation at the respective rotary joints is a friction cable or chain drive. Other friction drives such as a belt drive could also be used. The reduction ratios produced by the drive systems can range from 1:1 to 10,000:1.

As will be appreciated by those skilled in the art, six degrees of freedom are all that is required to define the position of the tool mount in space. Thus, the seventh degree of freedom provided by the exemplary manipulators shown in FIGS. 1-8 is a redundant degree of freedom. The redundant seventh degree of freedom provides for good torque delivery in a wider variety of orientations as compared to a manipulator having just six degrees of freedom (i.e., no redundant degrees of freedom) and expands the operational envelope beyond what many six degree of freedom manipulators can achieve. The range of motion of all hybrid serial/parallel mechanisms is defined by a series of singularity points where the manipulator becomes locked and can no longer move freely. At these singularity points, the manipulator becomes locked and can no longer move freely. These singularity points happen when the manipulator is at full extension with the mechanical elements of the manipulator binding against one another in such a way that the manipulator cannot provide enough force or torque to move itself and whatever tool is being manipulated.

For example, if the upper first actuator system 716 of the manipulator of FIG. 8 were limited to a two degree of freedom actuator system, the redundant degree of freedom would be eliminated and the degrees of freedom of the actuator systems would match up with the degrees of freedom available at the attachment point joints 726, 727. With the rotary joint/actuator 728 carried by the support member 712, the manipulator would have a total of six degrees of freedom. However, the ability of such a manipulator to create torque on the support member 712 is reduced as the line connecting the attachment points of the first and second actuator systems to the support member changes from a vertical to a more horizontal orientation. Specifically, the ability to create torque is reduced by the sine of the angle that the line connecting the two attachment points forms with a horizontal plane. As that angle, and the sine of that angle, approaches zero, the lever arm that could be used to create torque in the support arm approaches zero length. In such a situation, force can only be applied to the support member in the axial direction relative to the line connecting the attachment points. This restricts the work that can be done by the manipulator.

Adding a third degree of freedom to the first actuator system 716 helps alleviate this problem. In particular, the additional degree of freedom allows a force to be produced in a direction perpendicular, or at some other angle, relative to the line connecting the attachment points 726, 727. Thus, torque can be produced in any orientation of the support member 712.

For sensing the positions of the various rotary joints 754, 756, 764 on the manipulator and, in turn, the support member 712 and tool mount 714 all or some of the rotary joints can be equipped with position sensors. Each of the drive systems of the manipulator can be in communication with the controller and the position sensors can provide position information in a feedback loop to the controller. It will be appreciated that any number of different conventional position sensors can be used such as, for example, optical encoders. Moreover, the various drive systems can also be equipped with force sensors for sensing the forces or torques applied by the actuators so as to enable a determination of the forces and torques applied to the support member and/or the tool mount. This information can again be provided in a feedback control loop to the controller, for example to allow force feedback to the input device of a haptic interface. Of course, any known method for measuring forces and/or torques can be used, including, for example, foil type or semiconductor strain gauges or load cells.

Special control techniques are necessary when two or more of the drive systems of the joints/actuators 770, 774, 782 of the first and second actuator systems 716, 718 are coupled together in parallel through redundant application to drive the mechanism. In such situations, two or more drive systems may be supplying power to the same elements of the manipulator mechanism to accomplish the same movement. These situations occur because of the seventh redundant degree of freedom. The special control techniques that are necessary include methods to control torque and position when multiple drive systems, for example two drive systems, are supplying torque to an element of the manipulator at the same time. These methods can include sharing the load between the two drive systems according to a complex Jacobian transform relating the load in Cartesian space to joint torque. Alternatively, the load can be divided proportionally with one drive system serving as the position control master and with the other drive system serving as a force applying slave element. One of the redundant drive systems also could be allowed to rest so that its movement does not conflict with movement of the other drive system involved in moving the particular element of the manipulator mechanism. The most complex interactions between the various drive systems occur when the support member 712 and tool mount 714 are at an angle to the horizontal and the centerline of the manipulator mechanism planes. In this particular condition, all of the drive systems are interacting with one another. The Jacobian transform method is the preferred method for handling those complex interactions.

In view of the foregoing, it will be appreciated that the present invention provides a manipulator that provides seven degrees of freedom. The redundant seventh degree of freedom provides improved performance by improving torque delivery certain orientations and by helping to eliminate certain singularity points. Manipulators having first and second actuator systems with particular configurations are shown in the drawings and described herein. Of course, other types of three degree of freedom actuator systems could also be used. For example, each of the first and second actuator systems could be based on a so-called r-theta actuator systems, which is a two degree of freedom radial coordinate engine. A further actuator can then be connected to each r-theta mechanism which is able to independently move the corresponding r-theta mechanism out of its respective rotational plane. The result is that the first and second actuator systems are two independent three degree of freedom actuator systems. Other arrangements are also possible.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A manipulator for use in medical procedures comprising first and second actuator systems each including three or more powered actuators, each powered actuator being capable of actuating a separate movement of at least a portion of the respective actuator system without any movement of the other actuator system; a body for supporting a medical tool, the body being supported by the first and second actuator systems at first and second attachment points, respectively, such that the first and second actuator systems are capable of manipulating the body in five degrees of freedom in a medical procedure.

2. The manipulator of claim 1 further comprising a third actuator system having first and second ends, the first end attached to the body, wherein the second end is movable relative to the body with at least one degree of freedom.

3. The manipulator of claim 1 wherein both the first and second actuator systems comprise serial actuator systems.

4. The manipulator of claim 3 wherein each of the first and second actuator systems employs at least three rotary joint actuators.

5. A manipulator for use in medical procedures comprising first and second actuator systems each including three or more powered actuators with each of the three or more powered actuators being arranged in series relative to the others, each powered actuator being capable of actuating a separate movement of at least a portion of the respective actuator system without any movement of the other actuator system; a body supported by the first and second actuator systems at first and second attachment points, respectively, such that the first and second actuator systems are capable of manipulating the body in five degrees of freedom, wherein the first attachment point comprises a two degree of freedom joint and the second attachment point comprises a three degree of freedom joint; and a third actuator system having first and second ends, the first end attached to the body.

6. A manipulator for use in medical procedures comprising first and second actuator systems each including three or more powered actuators, each powered actuator being capable of actuating a separate movement of at least a portion of the respective actuator system without any movement of the other actuator system; a body supported by the first and second actuator systems at first and second attachment points, respectively, such that the first and second actuator systems are capable of manipulating the body in five degrees of freedom wherein the first attachment point comprises a two degree of freedom joint and the second attachment point comprises a three degree of freedom joint.

7. A manipulator for use in medical procedures comprising first and second actuator systems each including three or more powered actuators, each powered actuator being capable of actuating a separate movement of at least a portion of the respective actuator system without any movement of the other actuator system; a medical tool; a body for supporting the medical tool, the body being supported by the first and second actuator systems at first and second attachment points, respectively, such that the first and second actuator systems are capable of manipulating the body in five degrees of freedom in a medical procedure; and a third actuator system having first and second ends, the first end attached to the body, wherein the second end is movable relative to the body with at least one degree of freedom without any movement of either the first or the second actuator system.

8. A method for performing a medical procedure on a patient comprising the steps of:

supporting a medical tool on a body, supporting the body with first and second actuator systems at first and second attachment points, respectively, such that the first and second actuator systems are capable of manipulating the body in five degrees of freedom, the first and second actuator systems each including three or more powered actuators, each powered actuator being capable of actuating a separate movement of at least a portion of the respective actuator system without any movement of the other actuator system; and manipulating the body in up to five degrees of freedom with respect to the patient.

9. A method for performing a medical procedure on a patient comprising the steps of:

supporting a body with first and second actuator systems at first and second attachment points, respectively, such that the first and second actuator systems are capable of manipulating the body in five degrees of freedom, the first and second actuator systems each including three or more powered actuators, each powered actuator being capable of actuating a separate movement of at least a portion of the respective actuator system without any movement of the other actuator system;

supporting a medical tool on the body with a third actuator system, the third actuator system including a first end attached to the body and a second end configured to support the medical tool, wherein the second end is movable relative to the body with at least one degree of freedom without any movement of either the first or second actuator systems; and manipulating the body supporting the medical tool in up to five degrees of freedom with respect to the patient.

10. A method for performing a medical procedure on a patient comprising the steps of:

supporting a medical tool on a body, supporting the body with first and second actuator systems at first and second attachment points, respectively, such that the first and second actuator systems are capable of manipulating the body in five degrees of freedom, the first and second actuator systems each including three or more powered actuators, each powered actuator being capable of actuating a separate movement of at least a portion of the respective actuator system without any movement of the other actuator system, wherein the first attachment point comprises a two degree of freedom joint and the second attachment point comprises a three degree of freedom joint; and manipulating the body in up to five degrees of freedom with respect to the patient.

* * * * *